United States Patent [19]

Flannagan

[11] Patent Number: 5,338,195

[45] Date of Patent: Aug. 16, 1994

[54] DENTAL HANDPIECE SHROUD TO PROTECT AGAINST PERCUTANEOUS INJURY

[76] Inventor: Michael L. Flannagan, 1388 W. 31st St., Jasper, Ind. 47546

[21] Appl. No.: 21,761

[22] Filed: Feb. 24, 1993

Related U.S. Application Data

[63] Continuation of Ser. No. 826,447, Jan. 27, 1992, abandoned.

[51] Int. Cl.$^5$ .......................... A61C 1/16; A61G 15/00
[52] U.S. Cl. ......................................... 433/116; 433/77
[58] Field of Search ............................. 433/116, 28, 77

[56] References Cited

U.S. PATENT DOCUMENTS

| | | | |
|---|---|---|---|
| 1,275,847 | 8/1918 | Chertok | 433/116 |
| 2,835,084 | 5/1958 | Fotre | 433/116 X |
| 4,286,950 | 9/1981 | Hawk | 433/116 |
| 4,722,685 | 2/1988 | de Estrada | 433/116 X |
| 4,723,912 | 2/1988 | Nieusma | 433/116 |
| 4,789,336 | 12/1988 | Lewis | 433/116 |
| 4,810,194 | 3/1989 | Snedden | 433/91 |
| 4,880,381 | 11/1989 | Nieusma, Jr. | 433/28 |
| 4,884,968 | 12/1989 | Stein | 433/116 |
| 5,064,375 | 11/1991 | Jorneus | 433/116 X |

FOREIGN PATENT DOCUMENTS 182473 7/1955 Fed. Rep. of Germany .

OTHER PUBLICATIONS

Siew, et al., *Self-Reported Percutaneous Injuries in Dentists: Implications for HBV, HIV Transmission Risk:* 123 Journal of American Dental Association 37 (Jul. 1992).
Scarbeck, *Handpieces: The Latest Target For Infection Control*, 20 Academy of General Dentistry Impact 16 (Oct. 1992).
Miner, *Aesepis Special Report:* Public Concern over Health Hazards Force Closer Look at Dental Infection Control Procedures, Patterson today pp. 6–9 (Winter--Spring 1986).
Associated Bag Company, *Medical Products,* 1992 Medical Catalog (vol. 1).
Palco Dental Products, 1992/1993 Catalog, 57th Edition, particularly "Barriers" at pp. 3–5.
Robin Dental Company, Equipment & Supplies Fall 1992, p. 86 (feature carts, handpiece controls) and pp. 92–94 (Holder Brackets, Instruments Holder and Mouth Replacement Holders).
Henry Schein, Inc., *Dental '92* (Nov.–Dec. 1992), particularly p. 16, showing Cure Sleeve TM and H. P. Sleeve TM Approach to bur protection.
Patterson Dental Company, Year End Savings (Nov. 1992), particularly p. 18 showing hand piece products and p. 23 showing "barrier" products.
Patterson Dental Company, "Patterson Today" (Winter–Spring 1986), particularly pp. 14–15; 18–19; and 38–40.
Meer Dental "Word of Mouth" Catalog, particularly pp. 4 and 10.
Decade products catalog (excerpts, pp. 13–14, 17–18 and 21-22).
American Dental Accessories, Inc. Catalog (1993), particularly pp. 50–59.
Dental Products Report (Sep. 1992) pp. 96 and 105.
A-Dec Equipment Catalog (1990).
Dental Products Report (Nov. 1992, most recent complete catalog at time of submission in parent case).

*Primary Examiner*—Gene Mancene
*Assistant Examiner*—Nicholas D. Lucchesi
*Attorney, Agent, or Firm*—Middleton & Reutlinger

[57] ABSTRACT

A protective shroud for a dental handpiece having particular adaptability for encasing a bur-containing chuck on a handpiece to avoid percutaneous contact by the bur with an individual and the transfer of a contaminated substance, such as a virus. The protective shroud is provided with sufficient depth so that the bur of a dental handpiece is stored behind the leading edge of the shroud and does not protrude therefrom, thereby preventing accidental contact with the bur. The shroud is also provided with a cut-out portion, typically facing the direction of the dentist or dental technician, which permits grasping of the handpiece below the bur to effect ready withdrawal and return of the handpiece from and to the protective shroud while performing dental operations on a patient.

9 Claims, 1 Drawing Sheet

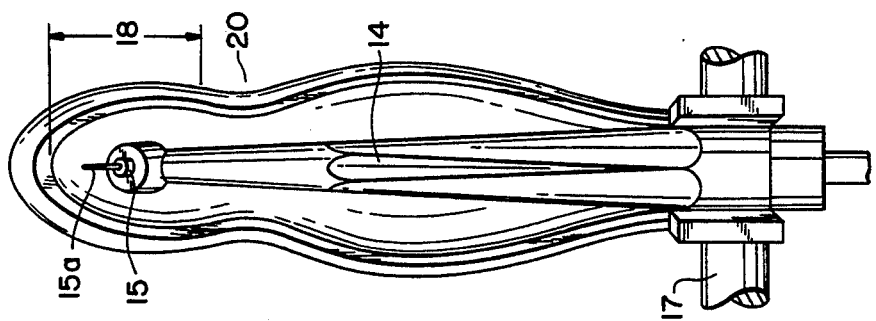
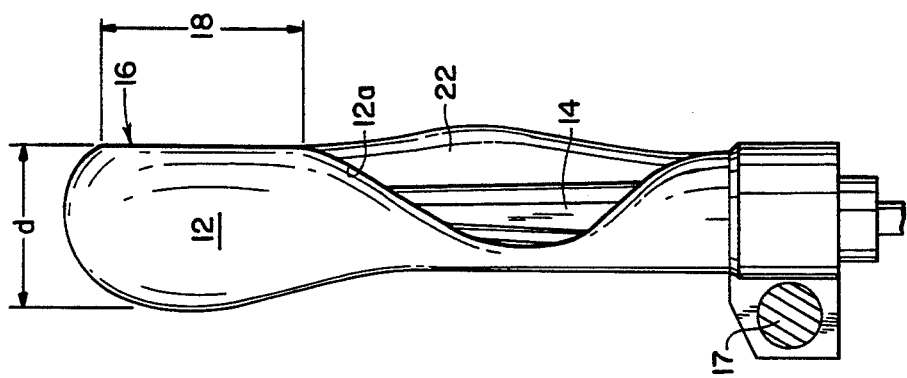
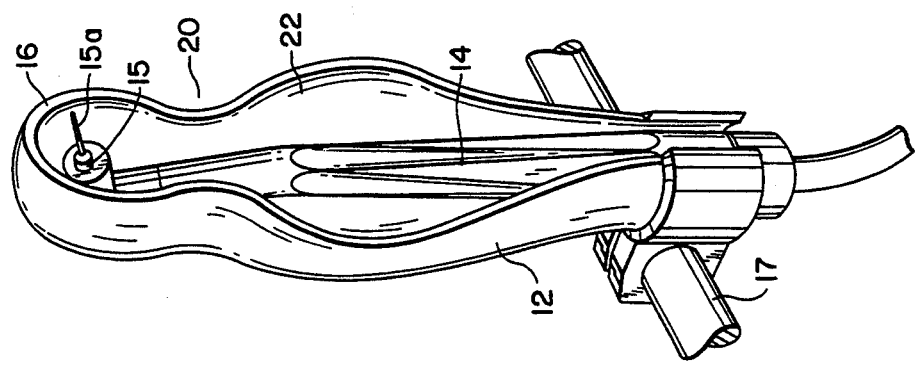

DENTAL HANDPIECE SHROUD TO PROTECT AGAINST PERCUTANEOUS INJURY

BACKGROUND OF THE INVENTION

This is a continuation of my earlier filed application, Ser. No. 07/826,447, filed Jan. 27, 1992, the disclosure of which is incorporated herein by reference.

As is known, the practice of dentistry involves the use of a variety of instruments, such as a dentist's drill (commonly referred to as the "handpiece"), a scaler or the like, and including the assistant's instruments as, for example, a saliva ejector. Typically, the preceding are arranged on a wheeled cart which is disposed in the region proximate the dentist, the assistant and the patient.

In recent years, attention has been focussed upon the practice of dentistry, particularly as it relates to the possibility of acquiring a number of infections, for example Acquired Immune Deficiency Syndrome (commonly referred to as "AIDS" and often referred to by the virus name "H-IV") and Hepatitis B (commonly referred to as "H-BV"), and other infectious diseases. Since the early 1980s, serious approaches have been undertaken to prevent H-IV virus transmission as, for example, the dentist and the dental assistant's usage of hand gloves and the like. Much of this sort of preventive procedure is now OSHA and/or professional organization prescribed.

Another response to prevent transmission of H-IV and/or H-BV viruses has concentrated on the bacteriocidal control of dental instruments, including sterilization of the instruments in an autoclave or the like, and then encasing the sterilized instrument(s) in bacteriocidal barriers, such as plastic wrap or the like, until the instrument(s) are needed for use in a dental procedure. A number of patents have addressed this approach: U.S. Pat. No.4,789,336 ("Lewis"); U.S. Pat. No. 4,880,381 ("Nieusma, Jr."); and U.S. Pat. No. 4,723,912 ("Nieusma").

An outstanding, and remaining, problem is in connection with the handpiece which has a chuck containing a projecting bur (i.e., that portion of the handpiece which actually engages and "drills" dental material). The aforesaid bur has a great propensity for vital contamination, and the typical storage thereof during use while servicing a dental patient, as on a rod on the aforementioned cart, leaves the dentist, the dental assistant, and/or even the patient at risk to unwanted physical contact with the bur. This can lead to skin puncturing (i.e., "percutaneous injury") because of the exposed bur of the handpiece.

The aforementioned patents which take a bacteriocidal approach to preventing H-IV or H-BV transmission do not adequately address the problem of percutaneous injury, because the bacteriocidal barriers are typically comprised of thin films of plastic or aluminum or the like, which thin film barriers are easily punctured or pierced by the bur of the handpiece. Thus, especially during use during dental procedures, the bur is exposed and capable of producing percutaneous injury. Indeed, according to a 1992 survey by the American Dental Association, contact with the bur of a handpiece was the leading cause of percutaneous injury.

BRIEF DESCRIPTION OF THE INVENTION

The present invention readily overcomes the preceding problem of percutaneous injury due to contact with a contaminated bur, by providing a substantially rigid shroud which fully encases the handpiece (including the protruding bur) while the dentist or assistant or hygienist is working on the patient's tooth, and otherwise. At the same time, the protective shroud permits ready access to the handpiece as required for continued dental activities.

In other words, and quite simply, a shroud, fabricated from firm rubber, plastic, a metallic material, a cellulose bearing material or the like, provides a protective shield to fully encase the bur and prevents accidental contact with the exposed bur. This effectively diminishes the chances of accidental skin puncturing and the passage of contaminated material on or from the bur to the punctured area.

DESCRIPTION OF THE FIGURES

A better understanding of the present invention will become more apparent from the following description, taken in conjunction with the accompanying drawing, wherein FIG. 1 is a perspectives view of a dental handpiece shroud in accordance with the teachings of the present invention and in a typically mounted position;

FIG. 2 is a view in side elevation of the invention, looking generally from left to right in FIG. 1; and, FIG. 3 is a view in front elevation further detailing the shroud of the invention.

For the purposes of promoting an understanding of the principles of the invention, reference will now be made to the embodiment illustrated in the drawing and specific language will be used to describe the same. It will nevertheless be understood that no limitation of the scope of the invention is thereby intended, such alterations and further modifications of the illustrated device and such further applications of the principles of the invention as illustrated therein being contemplated as would normally occur to one skilled in the art to which the invention relates.

DESCRIPTION OF THE PREFERRED EMBODIMENT

Referring now to the figures, the dental handpiece shroud 12 of the invention is shown in a typical use condition, i.e., on a rod 17 mounted on a conventional instrument cart positioned adjacent the dentist. As evident in each of the figures, the shroud 12 is adapted to receive a dental handpiece 14, including one with a bur 15a extending from the handpiece chuck 15. As shown most clearly in FIG. 2, the upper portion 18 of shroud 12 is provided of depth "d" so that leading edge 16 of shroud 12 always extends beyond bur 15a, and bur 15a does not protrude from the upper region 18 of shroud 12. Leading edge 16 is presented for a sufficient vertical length or distance 18, such that handpieces of varying lengths may be accommodated, yet still maintain bur 15a behind leading edge 16 to preclude contact with bur 15a.

Upper region 18 of shroud 12 is also presented in such fashion that the width 20 is sufficiently constricted so that the user will not come into contact with the handpiece 12 (particularly bur 15a) if the user accidently attempts to grasp handpiece 12 in the vicinity of upper region 18.

As can be seen, the arrangement of shroud 12 is such that the dentist, dental attendant and/or the patient cannot readily be placed into contact with the bur 15a, since the hand implement 14, including the bur 15a, is facing the dentist and is fully shielded behind the leading edge 16 of shroud 12. At the same time, because of open face 22 and the cut-out portion 12a, the dentist/dental assistant/hygienist is readily able to reach the handpiece in the area below upper region 18, as explained immediately hereafter.

As a way to expediency in use, the shroud 12 has a cut-out portion 12a to permit ready access by the dentist to the handpiece 14. Restated otherwise, effective concealment of the bur 15a held by the handpiece chuck 15 is assured in that the shroud 12 serves as effective shield from contact with bur 15a for at least the length of upper region 18 of leading edge 16 of the handpiece 14 and particularly that area where unintended physical contact would most likely occur.

The invention satisfies a serious existing need for the practitioner by being readily adaptable for ready and repeated access of the handpiece 14 during use on a patient: and, at the same time, is advantageously obstructive to accidental physical contact with bur 15a by the dental user.

The dental handpiece shroud described here above is susceptible to various changes within the spirit of the invention, including, by way of example, in proportioning: in the selection of material, including that identified as pliable, employed to fabricate the shroud the retaining of the dental handpiece in position: the precise arrangement for mounting the shroud at a use location: and, the like. Thus, the preceding should be considered illustrative and not as limiting the scope of the following claims:

I claim:

1. A protective shroud for a removable dental handpiece containing a bur and to protect against contact with said bur, comprising an elongated body having an open face extending substantially the length of said elongated body, a first end portion, a middle portion and a second end portion, wherein said first end portion is of sufficient depth from a leading open edge to the rear of said first end portion and further comprises means for receiving, fully encasing and retaining the portion of the handpiece containing said bur so that said bur does not protrude beyond said leading edge of said first end portion of said protective shroud.

2. The protective shroud of claim 1 where said first end portion is of restricted width to permit reception of said handpiece but not permit insertion of a dental operator's fingers.

3. The protective shroud of claim 1 wherein said middle portion includes a cutout portion to permit a dental operator to grasp said handpiece in a region other than the portion of said handpiece containing said bur, for selected placement, removal and replacement of said handpiece within said protective shroud.

4. The protective shroud of claim 3 wherein said protective shroud is adaptable to be received by a tray for dental instruments.

5. The protective shroud of claim 3 wherein said protective shroud is comprised of substantially rigid material.

6. The protective shroud of claim 5 wherein said substantially rigid material is plastic.

7. The protective shroud of claim 5 wherein said substantially rigid material is metallic.

8. The protective shroud of claim 5 wherein said substantially rigid material is comprised of cellulose-bearing material.

9. The protective shroud of claim 5 wherein said substantially rigid material is comprised of rubber.

* * * * *